United States Patent [19]

Ha et al.

[11] Patent Number: 5,053,529

[45] Date of Patent: Oct. 1, 1991

[54] PROCESS FOR THE PREPARATION OF N-PHOSPHONOMETHYLGLYCINE

[75] Inventors: Hyun-Joon Ha; Kyong Pae Park, both of Seoul, Rep. of Korea

[73] Assignee: Korea Institute of Science and Technology, Seoul, Rep. of Korea

[21] Appl. No.: 608,471

[22] Filed: Nov. 2, 1990

[30] Foreign Application Priority Data

May 25, 1990 [KR] Rep. of Korea ............... 7634/1990

[51] Int. Cl.$^5$ .................................. C07F 9/38
[52] U.S. Cl. ............................ 562/18; 558/115
[58] Field of Search ....................... 562/18; 558/115

[56] References Cited

U.S. PATENT DOCUMENTS 4,053,505 10/1977 Dutra .................................. 562/18
4,415,503 11/1983 Robbins .............................. 562/18
4,428,888 1/1984 Robbins .............................. 562/18

Primary Examiner—Bruce Gray

[57] ABSTRACT

There is disclosed a novel process for the preparation of N-phosphonomethylglycine of formula(I)

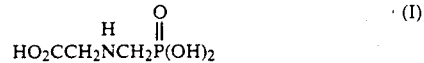

(wherein, R and R$^1$ are selected from the group consisting of alkyl having 1 to 2 carbon atoms) which process comprises reacting 1,3,5-tricarboalkoxymethylhexahydro-s-triazine with trialkylphosphite in the presence of titanium tetrachloride to form N-phosphonomethylglycine triester and converting the triester into a N-phosphonomethylglycine by saponification.

3 Claims, No Drawings

PROCESS FOR THE PREPARATION OF N-PHOSPHONOMETHYLGLYCINE

BACKGROUND OF THE INVENTION

The present invention relates to a novel method for the preparation of N-phosphonomethylglycine of formula (I), a herbicidal component which is known in the agricultural chemical art as glyphosate.

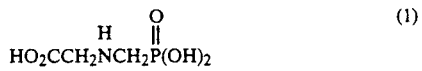

(1)

German Offen. No. 2,700,017 discloses a process for producing N-phosphonomethylglycine by a process in which 1,3,5-tricarboethoxymethylhexahydro-s-triazine is reacted with dialkylphosphite under reflux followed by hydrolysis. This process requires high reaction temperature for a few hours to react triazine with dialkyl-phosphite to make N-phosphonomethylglycine triesters. Furthermore, removal of high boiling solvent such as benzene, toluene etc. before hydrolysis also makes this process laborious. We now have discovered that a simple and mild process for the preparation of N-phosphonomethylglycine triesters. The present invention involves the preparation of N-phosphonomethylglycine triesters of the formula II by reacting ),3,5-tricarboalkoxymethylhexahydro-s-triazine of the formula III with trialkylphosphite of the formula IV in the presence of titanium tetrachloride and followed by hydrolysis to make N-phosphonomethylglycine of the formula I. The following reactions illustrate the present invention;

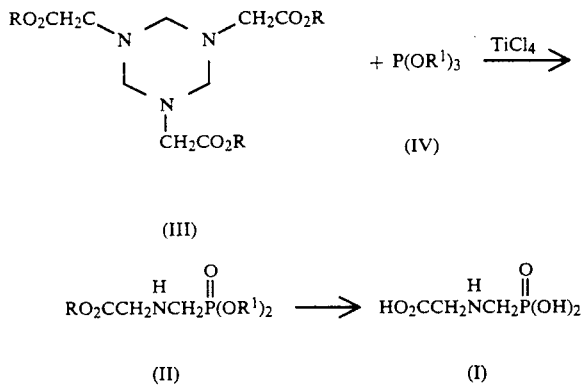

Wherein, R and $R^1$ are selected from the group consisting of alkyl having 1 to 2 carbon atoms which is inert to the coupling reaction Titanium tetrachloride is added into 1,3,5-tricarboalkoxymethylhexahydro-s-triazine in proper solvent to give dark yellow colored solution at $-10$–$0°$ C. Into this solution was added trialkylphosphite and the resulting reaction mixture was stirred at the same temperature. Without titanium tetrachloride the reaction has not proceeded at all. The amount of titanium tetrachloride is 3–3.5 mole equivalents to 1,3,5-tricarboalkoxymethylhexahydro s-triazine. The solvent for the reaction is any one of methylene chloride, chloroform, carbon tetrachloride, trichloroethylene without affecting the reaction yield The way to carry out the reaction is that 3.5 mole equivalent of titanium tetrachloride is added to one more equivalent of 1,3,5-tricarboalkoxymethylhexahydro-s-triazine followed by addition of 3 mole equivalent of trialkylphosphite at $-10$–$0°$ C. In case of large scale reaction, portionwise addition of reactants is recommended to control the reaction temperature. At first 1.5 mole equivalent of titanium tetrachloride was added into 1 mole equivalent of 1,3,5-tricarboalkoxymethylhexahydro-s-triazine in proper solvent followed by addition of 1 mole equivalent of trialkylphosphite. Then 1 mole equivalent of titanium tetrachloride was added followed by addition of another 1 mole equivalent of trialkylphosphite. Finally residual one mole equivalent of titanium tetrachloride and one mole equivalent of trialkylphosphite were added.

The present invention relates to a process for hydrolysis of N-phosphonomethylglycine triesters with aqueous inorganic acids such as hydrochloric acid, sulfuric acid, or hydrobromic acid. Using volatile acid such as hydrochloric acid or hydrobromic acid has an advantage to be concentrated under reduced pressure easily after hydrolysis. Therefore, hydrolysis of N-phosphonomethylglycine triesters with hydrochloric acid or hydrobromic acid under reflux to give white solid N-phosphonomethylglycine. Hydrolysis of N-phosphonomethylglycine triesters is also carried out at $80$–$100°$ C. for 2 hours with aqueous hydroxide solution such as NaOH or KOH. The final product N-phosphonomethylglycine was obtained after acidification of its salt obtained from the hydrolysis with aqueous hydroxide solution.

1,3,5-tricarboalkoxymethylhexahydro-s-triazine used in this invention was obtained from the reaction of glycine alkoxyester with formaldehyde.

All of the products in this invention were fully identified by elemental analysis and spectrometry.

The following examples illustrate the process of the invention in more detail.

EXAMPLE 1

To 1,3,5-tricarboethoxymethylhexahydro-s-triazine (2.07g, 6mmol) in 50ml of methylene chloride at $-10$–$0°$ C. was added slowly titanium tetrachloride (4.0 g, 21 mmol), and the mixture was stirred for 10 minutes at $0°$ C. To the resulting solution was added triethylphosphite (2.9 g, 18 mmol). This reaction mixture was stirred at $-10$–$10°$ C. for 1 hour. After the reaction was completed it was poured into 10 ml of water. After the solution was neutralized by saturated $NaHCO_3$ solution the reaction product was extracted by methylene chloride. After the removal of solvent 2.96 g of N-phosphonomethylglycine triester (R=, $C_2H_5$, $R^1=C_2H_5$) was obtained in 65% yield.

EXAMPLE 2

Saponification was carried out by heating a solution of 1.27 g of N-phosphonomethylglycine triester (R=$C_2H_5$. $R^1=C_2H_5$) obtained in example 1 with 5.2 ml of concentrated hydrochloric acid for 2 hours under reflux. After the reaction was completed the reaction mixture was concentrated and recrystallized from water to give 0.6 g of N-phosphonomethylglycine as white solid with boiling point $233$–$235°$ C. in 71% yield.

m.p.($°$ C.) (decomp.): $234 \pm 1°$ C.

NMR ($D_2O$, ppm) : $\delta 3.23$ (d, J=12Hz, 2H, —NCH P—) $\delta 4.03$ (s, 2H, —CCH N—)

IR(KBr) : $\nu OH$: $3300 cm^{-1}$ $\mu C=O$: $1734 cm^{-1}$ $\mu P=O$: $1244 cm^{-1}$

EXAMPLE 3

In example 1, while otherwise proceeding as described but substituting an equimolar quantity of trimethylphosphite for triethylphosphite, N-phosphonomethylglycine triester (R=$C_2H_5$, $R^1$=$CH_3$) was obtained in 92% yield.

EXAMPLE 4

In example 2, while otherwise proceeding as described but substituting an equimolar quantity of N-phosphonomethylglycine triester (R=$C_2H_5$, $R^1$=$CH_3$) obtained in example 3 for N-phosphonomethylglycine triester (R=$C_2R_5$, $R^1$=$C_2H_5$) obtained in example 1, N-phosphonomethylglycine was obtained in 75% yield.

What is claimed is:

1. A process for the preparation of N-phosphonomethylglycine of the formula (I) which comprises the steps of a reacting 1,3,5-tricarboalkoxymethylhexahydro-s-triazine of the formula (III) with trialkylphosphite of the formula (IV) in the presence of titanium tetrachloride to form N-phosphonomethylglycine triester of the formula (II), and b. converting the triesters into a corresponding acid N-phosphonomethylglycine by saponification,

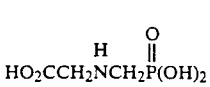

(I)

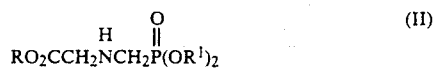

(II)

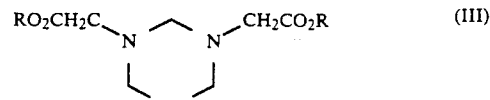

(III)

$P(OR^1)_3$ (IV)

wherein R and $R^1$ represent methyl or ethyl, respectively.

2. The process of claim 1 wherein the mole ratio of 1,3,5-tricarboalkoxymethylhexahydro-s-triazine, titanium tetrachloride and trialkylphosphite is 1:3–3.5:3.

3. The process of claim 1 wherein the step (a) for the preparation of N-phosphonomethylglycine triester comprises using methylene chloride, chloroform, carbon tetrachloride, or trichloroethylene as solvent.

* * * * *